US007556919B2

(12) United States Patent
Chenchik et al.

(10) Patent No.: US 7,556,919 B2
(45) Date of Patent: Jul. 7, 2009

(54) LONG OLIGONUCLEOTIDE ARRAYS

(75) Inventors: Alex Chenchik, Palo Alto, CA (US); Alexander Munishkin, Santa Cruz, CA (US); Peter Simonenko, Mountain View, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 315 days.

(21) Appl. No.: 10/985,372

(22) Filed: Nov. 9, 2004

(65) Prior Publication Data

US 2006/0068403 A1 Mar. 30, 2006

Related U.S. Application Data

(62) Division of application No. 09/440,829, filed on Nov. 15, 1999, now Pat. No. 7,041,445.

(51) Int. Cl.
*C12Q 1/68* (2006.01)
*C12N 11/16* (2006.01)
*G01N 15/06* (2006.01)

(52) U.S. Cl. .................. 435/6; 435/283.1; 435/287.2; 422/68.1; 536/23.1

(58) Field of Classification Search .................. None
See application file for complete search history.

(56) References Cited

U.S. PATENT DOCUMENTS

| | | | |
|---|---|---|---|
| 5,436,327 A | | 7/1995 | Southern et al. |
| 5,445,934 A | * | 8/1995 | Fodor et al. ................. 435/6 |
| 5,556,752 A | | 9/1996 | Lockhart et al. |
| 5,610,287 A | | 3/1997 | Nikiforov et al. |
| 5,667,972 A | | 9/1997 | Drmanac et al. |
| 5,688,642 A | | 11/1997 | Chrisey et al. |
| 5,695,940 A | | 12/1997 | Drmanac et al. |
| 5,700,637 A | | 12/1997 | Southern |
| 5,707,801 A | | 1/1998 | Bresser et al. |
| 5,744,305 A | | 4/1998 | Fodor et al. |
| 5,800,992 A | | 9/1998 | Fodor et al. |
| 5,807,522 A | | 9/1998 | Brown et al. |
| 5,830,645 A | | 11/1998 | Pinkel et al. |
| 5,994,076 A | * | 11/1999 | Chenchik et al. ............ 435/6 |
| 6,037,127 A | * | 3/2000 | Ebersole et al. ............. 435/6 |
| 6,271,002 B1 | | 8/2001 | Linsley et al. |
| 6,326,489 B1 | * | 12/2001 | Church et al. .............. 536/25.3 |
| 6,352,829 B1 | * | 3/2002 | Chenchik et al. ............ 435/6 |
| 6,383,749 B2 | * | 5/2002 | Bochkariov et al. ......... 435/6 |
| 6,506,594 B1 | | 1/2003 | Barany et al. |
| 6,548,021 B1 | | 4/2003 | Church et al. |

FOREIGN PATENT DOCUMENTS

| | | |
|---|---|---|
| EP | 0373203 B1 | 8/1994 |
| GB | 2318791 A | 5/1998 |
| WO | WO 93/17126 | 9/1993 |

OTHER PUBLICATIONS

U. Alon et al. "Broad Patterns of Gene Expression Revealed by Clustering Analysis of Tumor and Normal Colon Tissues Probed by Oligonucleotide Arrays," (1999) *Proc. Natl. Acad Sci. USA*, 96:6745-6750.
Beier et al. "Versatile Derivatisation of Solid Support Media for Covalent Bonding on DNA Microchips," (1999) *Nucleic Acids Research*, 27(9):1970-1977.
Bonnet et al. "Thermodynamic Basis of the Enhanced Specificity of Structured DNA Probes," (1999) *Proc. Natl. Acad. Sci. USA*, 96:6171-6176.
Chalifour et al. "A Method for Analysis of Gene Expression Patterns," (1994) *Analytical Biochemistry* 216:299-304.
Chen et al. "Analysis of Internal (n-1)mer Deletion Sequences in Synthetic Oligodeoxyribonucleotides by Hybridization to an Immobilized Probe Array," (1999) *Nucleic Acids Research*, 27(2):389-395.
Gerhold et al. "DNA Chips: Promising Toys Have Become Powerful Tools," (1999) *TIBS 24*, 168-173.
D. Graves "Powerful Tools for Genetic Analysis Come of Age," (1999) *Tibtech*, 17:127-134.
Gunderson et al. "Mutation Detection by Ligation to Complete n-mer DNA Arrays," (1998) *Genome Research*, 8:1142-1153.
Maldonado-Rodriguez et al. "Mutation Detection by Stacking Hybridization on Genosensor Arrays," (1999) *Molecular Biotechnology*, 11:13.
Mir et al. "Determining the Influence of Structure on Hybridization Using Oligonucleotide Arrays", (1999) *Nature Biotechnology*, 17:788-792.
G. Ramsay "DNA Chips: State-of-the Art," (1998) *Nature Biotechnology*, 16:40-44.
Sohail et al. "The Folding of Large RNAs Studied by Hybridization to Arrays of Complementary Oligonucleotides," (1999) *RNA*, 5:646-655.
Southern et al. (1999) "Molecular Interactions on Microarrays," (1999) *Nature Genetics Supplement*, 21:5-9.
Benotmane et al. "Noniosotopic Quantitative Analysis of Protein-DNA Interactions at Equilibrium," (1997) *Anal. Biochemistry*, 250:181-185.

(Continued)

*Primary Examiner*—B J Forman
(74) *Attorney, Agent, or Firm*—Bozicevic, Field & Francis, LLP; Bret E. Field

(57) ABSTRACT

Long oligonucleotide arrays, as well as methods for their preparation and use in hybridization assays, are provided. The subject arrays are characterized in that at least a portion of the probes of the array, and usually all of the probes of the array, are long oligonucleotides, e.g. oligonucleotides having a length of from about 50 to 120 nt. Each long oligonucleotide probe on the array is preferably chosen to exhibit substantially the same high target binding efficiency and substantially the same low non-specific binding under conditions in which the array is employed. The subject arrays find use in a number of different applications, e.g. differential gene expression analysis.

13 Claims, 1 Drawing Sheet

OTHER PUBLICATIONS

Fisher et al. "Real-Time DNA Binding Measurements of the ETS1 Recombinant Oncoproteins Reveal Significant Kinetic Differences Between the P42 and P51 Isoforms," 91994) *Protein Science*, 3:257-266.

Hibma et al. "A Non-Radioactive Assay for the Detection and Quantitation of A DNA Binding Protein," (1994) *Nucleic Acids Research*, 22(18):3806-3807.

* cited by examiner

LONG OLIGONUCLEOTIDE ARRAYS

TECHNICAL FIELD

The field of this invention is nucleic acid arrays.

BACKGROUND OF THE INVENTION

Nucleic acid arrays have become an increasingly important tool in the biotechnology industry and related fields. Nucleic acid arrays, in which a plurality of nucleic acids are deposited onto a solid support surface in the form of an array or pattern, find use in a variety of applications, including drug screening, nucleic acid sequencing, mutation analysis, and the like. One important use of nucleic acid arrays is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared.

In methods of differential gene expression, arrays find use by serving as a substrate to which is bound nucleic acid "probe" fragments. One then obtains "targets" from at least two different cellular sources which are to be compared, e.g. analogous cells, tissues or organs of a healthy and diseased organism. The targets are then hybridized to the immobilized set of nucleic acid "probe" fragments. Differences between the resultant hybridization patterns are then detected and related to differences in gene expression in the two sources.

A number of different physical parameters of the array which is used in such assays can have a significant effect on the results that are obtained from the assay. One physical parameter of nucleic acid arrays that can exert a significant influence over the nature of the results which are obtained from the array is probe size, i.e. the length of the individual probe nucleic acids stably associated with the surface of the solid support in the array. There are generally two different types of arrays currently finding use—(1) cDNA arrays, in which either full length or partial cDNAs are employed as probes; and (2) oligonucleotide arrays, in which probes of from about 8 to 25 nucleotides are employed.

In currently used cDNA arrays, the double stranded cDNAs which may be substantially full length or partial fragments thereof are stably associated with the surface of a solid support, e.g. nylon membrane. Advantages of cDNA arrays include high sensitivity, which features stems from the high efficiency of binding of the cDNA probe to its target and the stringent hybridization and washing conditions that may be employed with such arrays. Disadvantages of cDNA arrays include difficulties in large scale production of such arrays, low reproducibility of such arrays, and the like.

The other current alternative, oligonucleotide arrays, employs oligonucleotide probes in which each probe ranges from about 8 to 25, usually 20 to 35 nucleotides in length. While such arrays are more amenable to large scale production, they suffer from disadvantages as well. One significant disadvantage for such arrays is their lower sensitivity for target nucleic acids, as compared to cDNA arrays. Another disadvantage is the wide variation in hybridization efficiency of different probes for the same target in a given protocol, which feature requires the use of multiple oligonucleotide probes for the same target, which redundancy adds significantly to the cost of producing such arrays.

As such, there is a continued interest in the development of new array formats. Of particular interest would be the development of array format which combined the high sensitivity of cDNA arrays with the high throughput manufacturability of oligonucleotide arrays, where the format would not suffer from the disadvantages experienced with cDNA and oligonucleotide arrays, as described above.

RELEVANT LITERATURE

Patents and patent applications of interest include: U.S. Pat. Nos. 5,143,854; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,503,980; 5,510,270; 5,525,464; 5,527,681; 5,529,756; 5,545,531; 5,547,839; 5,554,501; 5,556,752; 5,561,071; 5,580,726; 5,580,732; 5,599,695; 5,599,672; 5,610;287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; WO 93/17126; WO 95/11995; WO 95/21265; WO 95/21944; WO 95/35505; WO 96/31622; WO 97/10365; WO 97/27317; WO 99/09217 WO 99/35505; EP 373 203; EP 742 287; EP 785 280; EP 799 897 and UK 8 803 000. References of interest include: Southern, et al. Nature Genet. (1999) 21:5-9; Sohail, et al., RNA (1999) 5:646-655; Mir et al., Nature Biotech. (1999)17: 788-792; Beier, et al., Nucl. Acids Res. (1999) 27:1970-1977; Rogers, et al., Anal. Biochem. (1999) 266:23-30; Vasiliskov, et al. BioTechniques (1999) 27:592-606; Chen, et al., Nucl. Acids Res. (1999) 27:389-395; Maldonado-Rodriguez, et al., Molec. Biotech. (1999) 11:13-25; Lipshutz, et al., Nature Genet. 1999, 21:20-24; Alon, et al., Proc. Natl. Acad. Sci. (1999) 96:6745-6750; Gunderson, et. al., Genome Research (1998) 8:1142-1153; Gilles et al., Nature Biotech. (1999) 17:365-370; Duggan, et al., Nature Genet. (1999) 21:10-14, Brown, P. O., Nature Genet (1999) 21:33-37; Pollack, et al., Nature Genet. (1999) 23:41-46; Wang et al., Gene (1999) 229:101-108; Bowtell, Nature Genet. (1999) 21:25-32; Schena, et al., TIBS (1998) 16:301-306; Debouck et al., Nature Genet. (1999) 21:48-50; The Microarray Meeting. Technology, Application and Analysis. Mountain Shadows Marriott Resort Scottsdale, Arizona, Sep. 22-25, 1999. Abstracts: 6-85; Gerhold et al., Trends in Biochem. Sciences. (1999) 24:168-173; Graves et al., Trends in Biotech. (1999) 17:127-134; Ekins et al., Trends in Biotech. (1999) 17:217-218; Atlas Human cDNA Expression Array I (April 1997) CLONTECHniques XII: 4-7; Lockhart et al., Nature Biotechnology (1996) 14: 1675-1680; Shena et al., Science (1995) 270: 467-470; Schena et al., Proc. Nat'l Acad. Sci. USA (1996)93:10614-10619; and Chalifour et al., Anal. Biochem. (1994) 216:299-304.

SUMMARY OF THE INVENTION

Long oligonucleotide arrays, as well as methods for their preparation and use in hybridization assays, are provided. The subject arrays are characterized in that at least a portion of the probes of the array, and usually all of the probes of the array, are long oligonucleotides, e.g. oligonucleotides having a length of from about 50 to 120 nt. Each long oligonucleotide probe on the array is preferably chosen to exhibit high target binding efficiency and low non-specific binding under conditions in which the array is employed, e.g. stringent hybridization conditions. In many embodiments, the specific probe oligonucleotides are chosen so that they have substantially the same hybridization efficiency to their respective targets.

The subject arrays find use in a number of different applications, e.g. differential gene expression analysis.

DEFINITIONS

Figure 1:
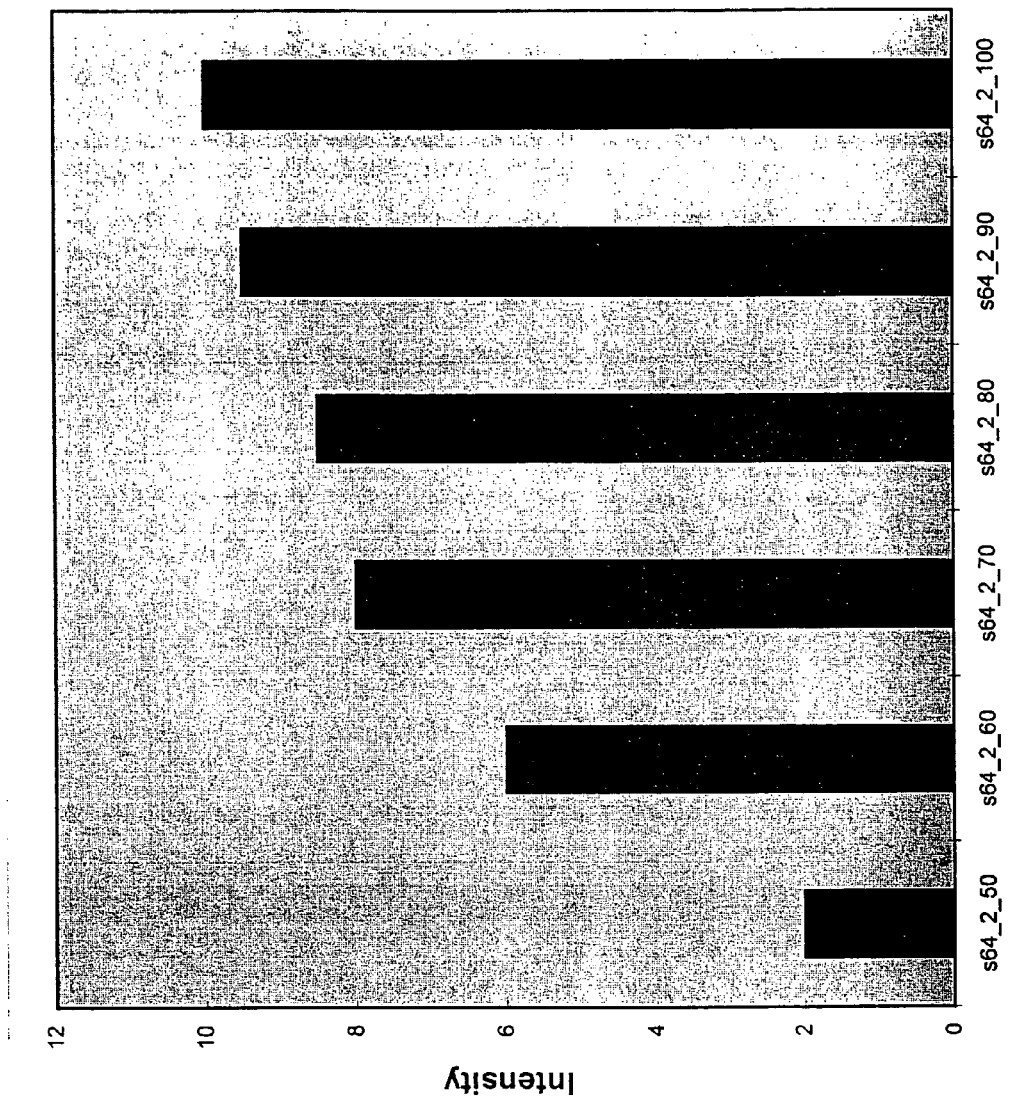
FIG. 1 provides a graphical representation of the hybridization efficiency of different length oligonucleotides.

The term "nucleic acid" as used herein means a polymer composed of nucleotides, e.g. naturally occurring deoxyribonucleotides or ribonucleotides, as well as synthetic mimetics thereof which are also capable of participating in sequence specific, Watson-Crick type hybridization reactions, such as is found in peptide nucleic acids, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "short oligonucleotide" as used herein denotes single stranded nucleotide multimers of from about 8 to 50 nucleotides in length, i.e. 8 to 50 mers.

The term "long oligonucleotide" as used herein denotes single stranded nucleotide multimers of from about 50 to 150, usually from about 50 to 120, nucleotides in length, e.g. a 50 to 150 mer, 50 to 120 mer, etc.

The term "polynucleotide" as used herein refers to single or double stranded polymer composed of nucleotide monomers of greater than about 150 nucleotides in length up to about 5000 nucleotides in length.

The term "oligonucleotide probe composition" refers to the nucleic acid composition that makes up each of the probes spots on the array that correspond to a target nucleic acid. Thus, oligonucleotide probe compositions of the subject arrays are nucleic acid compositions of a plurality of long oligonucleotides, where the composition may be homogenous or heterogenous with respect to the long oligonucleotides that make up the probe composition, i.e. each of the long oligonucleotides in the probe composition may have the same sequence such that they are identical or each of the probe compositions may be made up of two or more different long oligonucleotides that differ from each other in terms of sequence.

The term "target nucleic acid" means a nucleic acid for which there is one or more corresponding oligonucleotide probe compositions, i.e. probe oligonucleotide spots, present on the array. The target nucleic acid may be represented by one or more different oligonucleotide probe compositions on the array. The target nucleic acid is a nucleic acid of interest in a sample being tested with the array, where by "of interest" is meant that the presence or absence of target in the sample provides useful information, e.g. unique and defining characteristics, about the genetic profile of the cell(s) from which the sample is prepared. As such, target nucleic acids are not housekeeping genes or other types of genes which are present in a number of diverse cell types and therefore the presence or absence of which does not provide characterizing information about a particular cell's genetic profile.

The terms "background" or "background signal intensity" refers to hybridization signals resulting from non-specific binding of labeled target to the substrate component of the array. Background signals may also be produced by intrinsic fluorescence of the array components themselves. A single background signal can be calculated for the entire array, or a different background signal may be calculated for each target nucleic acid.

The term "non-specific hybridization" refers to the non specific binding or hybridization of a target nucleic acid to a nucleic acid present on the array surface, e.g. a long oligonucleotide probe of a probe spot on the array surface, a nucleic acid of a control spot on the array surface, and the like, where the target and the probe are not substantially complementary.

DESCRIPTION OF THE SPECIFIC EMBODIMENTS

Long oligonucleotide arrays, as well as methods for their preparation and use in hybridization assays, are provided. The subject arrays are characterized in that at least a portion or fraction, usually a majority of or substantially all of the probes of the array, and usually all of the probes of the array, are long oligonucleotides, e.g. oligonucleotides having a length of from about 50 to 120 nt. Each long oligonucleotide probe on the array is preferably chosen to exhibit high target binding efficiency and low non-specific hybridization under conditions in which the array is employed, e.g. stringent conditions. In certain embodiments, the arrays are further characterized in that each of the distinct probes on the array has substantially the same hybridization efficiency for its respective target. The subject arrays find particular use in gene expression assays. In further describing the subject invention, the arrays will first be described in general terms. Next, methods for their preparation are described. Following this description, a review of representative applications in which the subject arrays may be employed is provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Arrays of the Subject Invention—General Description

The arrays of the subject invention have a plurality of probe spots stably associated with a surface of a solid support. A feature of the subject arrays is that at least a portion of the probe spots, and preferably substantially all of the probe spots on the array are probe oligonucleotide spots, where each probe oligonucleotide spot on the array comprises an oligonucleotide probe composition made up of a plurality of long oligonucleotides of known identity, usually of known sequence, as described in greater detail below.

Probe Spots of the Arrays

As mentioned above, a feature of the subject invention is the nature of the probe spots, i.e. that at least a portion of, and usually substantially all of, the probe spots on the array are made up of probe nucleic acid compositions of long oligonucleotides. Each probe spot on the surface of the substrate is made up of long oligonucleotide probes, where the spot may be homogeneous with respect to the nature of the long oligonucleotide probes present therein or heterogenous, e.g. as described in U.S. Patent Application Ser. No. 60/104,179, the disclosure of which is herein incorporated by reference. A feature of the oligonucleotide probe compositions is that the probe compositions are made up of long oligonucleotides. As such, the oligonucleotide probes of the probe compositions range in length from about 50 to 150, typically from about 50 to 120 nt and more usually from about 60 to 100 nt, where in many preferred embodiments the probes range in length from about 65 to 85 nt.

In addition to the above length characteristics, the long oligonucleotide probes that make up the probe spots in the above are typically characterized by one or more of the following features in many preferred embodiments of the subject invention. One further characterization of the long oligonucleotides probes that make up the subject arrays is that their sequence is chosen to provide for high binding efficiency to their complementary target under stringent conditions. Binding efficiency refers to the ability of the probe to bind to its target under the hybridization conditions in which the array is used. Put another way, binding efficiency refers to the duplex yield obtainable with a given probe and its target after performing a hybridization experiment. In many embodiments, the probes present on the array surface that exhibit high binding efficiency having a binding efficiency for their target of 0.1%, usually at least 0.5% and more usually at least 2%.

Furthermore, the sequence of the long oligonucleotide probes is chosen to provide for low non-specific hybridization or non-specific binding, i.e. unwanted cross-hybridization, to target nucleic acids for which the probes are not substantially complementary under stringent conditions. A give target is considered to be substantially non-complementary to a given probe in the target has homology to the probe of less than 60%, more commonly less than 50% and most commonly less than 40%, as determined using the BLAST program with default settings. In certain embodiments, oligonucleotide probes having low non-specific hybridization characteristics and finding use in the subject arrays are those in which their relative ability to hybridize to non-complementary nucleic acids, i.e., other targets for which they are not substantially complementary, is less 10%, usually less than 5% and preferably less than 1% of their ability to bind to their complementary target. For example, in a side-by-side hybridization assay, probes having low non-specific hybridization characteristics are those which generate a positive signal, if any, when contacted with a target composition that does not include a complementary target for the probe, that is less than about 10%, usually least than about 3% and more usually less than about 1% of the signal that is generated by the same probe when it is contacted with a target composition that includes a complementary target.

In addition, the long oligonucleotides of a given spot are chosen so that each long oligonucleotide probe present on the array, or at least its target specific sequence, is not homologous with any other distinct unique long oligonucleotide present on the array, i.e. any other oligonucleotide probe on the array with a different base sequence. In other words, each distinct oligonucleotide of a probe composition corresponding to a first target does not cross-hybridize with, or have the same sequence as, any other distinct unique oligonucleotide of any probe composition corresponding to a different target, i.e. an oligonucleotide of any other oligonucleotide probe composition that is represented on the array. As such, the sense or anti-sense nucleotide sequence of each unique oligonucleotide of a probe composition will have less than 90% homology, usually less than 70% homology, and more usually less than 50% homology with any other different oligonucleotide of a probe composition corresponding to a different target of the array, where homology is determined by sequence analysis comparison using the FASTA program using default settings. The sequence of unique oligonucleotides in the probe compositions are not conserved sequences found in a number of different genes (at least two), where a conserved sequence is defined as a stretch of from about 15 to 150 nucleotides which have at least about 90% sequence identity, where sequence identity is measured as above.

The oligonucleotides of each probe composition, or at least the portion of these oligonucleotides that is complementary to their intended targets, i.e. their target specific sequences, are further characterized as follows. First, they have a GC content of from about 35% to 80%, usually between about 40 to 70%. Second, they have a substantial absence of: (a) secondary structures, e.g. regions of self-complementarity (e.g. hairpins), structures formed by intramolecular hybridization events; (b) long homopolymeric stretches, e.g. polyA stretches, such that in any give homopolymeric stretch, the number of contiguous identical nucleotide bases does not exceed 5; (c) long stretches characterized by or enriched by the presence of repeating motifs, e.g GAGAGAGA, GAAGAGAA, etc.; (d) long stretches of homopurine or homopyrimidine rich motifs; and the like.

The long oligonucleotide probes of the subject invention may be made up solely of the target specific sequence as described above, e.g. sequence designed or present which is intended for hybridization to the probe's corresponding target, or may be modified to include one or more non-target complementary domains or regions, e.g. at one or both termini of the probe, where these domains may be present to serve a number of functions, including attachment to the substrate surface, to introduce a desired conformational structure into the probe sequence, etc. One optional domain or region that may be present at one or more both termini of the long oligonucleotide probes of the subject arrays is a region enriched for the presence of thymidine bases, e.g. an oligo dT region, where the number of nucleotides in this region is typically at least 3, usually at least 5 and more usually at least 10, where the number of nucleotides in this region may be higher, but generally does not exceed about 25 and usually does not exceed about 20, where at least a substantial proportion of, if not all of, the nucleotides in this region include a thymidine base, where by substantial proportion is meant at least about 50, usually at least about 70 and more usually at least about 90 number % of all nucleotides in the oligo dT region. Certain probes of this embodiment of the subject invention, i.e. those in which the T enriched domain is an oligo dT domain, may be described by the following formula:

$$T_n\text{-}N_m\text{-}T_k;$$

wherein:

T is dTMP;

$N_m$ is the target specific sequence of the probe in which N is either dtMP, dGMP, dCMP or dAMP and m is from 50 to 100; and n and k are independently from 0 to 15, where when present n and/or k are preferably 5 to 10.

In yet other embodiments and often in addition to the above described T enriched domains, the subject probes may also include domains that impart a desired constrained structure to the probe, e.g. impart to the probe a structure which is fixed or has a restricted conformation. In many embodiments, the probes include domains which flank either end of the target specific domain and are capable of imparting a hairpin loop structure to the probe, whereby the target specific sequence is held in confined or limited conformation which enhances its binding properties with respect to its corresponding target during use. In these embodiments, the probe may be described by the following formula:

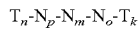
$$T_n\text{-}N_p\text{-}N_m\text{-}N_o\text{-}T_k$$

wherein:

T is dTMP;

N is dTMP, dGMP, dCMP or dAMP;

m is an integer from 50 to 100;

n and k are independently from 0 to 15, where when present n and/or k are preferably 5 to 10, where in many embodiments k=n=5 to 10, more preferably 10; and p and o are independently 5 to 20, usually 5 to 15, and more usually about 10, wherein in many embodiments p=o=5 to 15 and preferably 10;

such that $N_m$ is the target specific sequence; and $N_o$ and $N_p$ are self complementary sequences, e.g. they are complementary to each other, such that under hybridizing conditions the probe forms a hairpin loop structure in which the stem is made up of the $N_o$ and $N_p$ sequences and the loop is made up of the target specific sequence, i.e. $N_m$.

The oligonucleotide probe compositions that make up each oligonucleotide probe spot on the array will be substantially, usually completely, free of non-nucleic acids, i.e. the probe compositions will not include or be made up of non-nucleic acid biomolecules found in cells, such as proteins, lipids, and polysaccharides. In other words, the oligonucleotide spots of the arrays are substantially, if not entirely, free of non-nucleic acid cellular constituents.

The oligonucleotide probes may be nucleic acid, e.g. RNA, DNA, or nucleic acid mimetics, e.g. nucleic acids that differ from naturally occurring nucleic acids in some manner, e.g. through modified backbones, sugar residues, bases, etc., such as nucleic acids comprising non-naturally occurring heterocyclic nitrogenous bases, peptide-nucleic acids, locked nucleic acids (see Singh & Wengel, Chem. Commun. (1998) 1247-1248); and the like. In many embodiments, however, the nucleic acids are not modified with a functionality which is necessary for attachment to the substrate surface of the array, e.g. an amino functionality, biotin, etc.

The oligonucleotide probe spots made up of the long oligonucleotides described above and present on the array may be any convenient shape, but will typically be circular, elliptoid, oval or some other analogously curved shape. The total amount or mass of oligonucleotides present in each spot will be sufficient to provide for adequate hybridization and detection of target nucleic acid during the assay in which the array is employed. Generally, the total mass of oligonucleotides in each spot will be at least about 0.1 ng, usually at least about 0.5 ng and more usually at least about 1 ng, where the total mass may be as high as 100 ng or higher, but will usually not exceed about 20 ng and more usually will not exceed about 10 ng. The copy number of all of the oligonucleotides in a spot will be sufficient to provide enough hybridization sites for target molecule to yield a detectable signal, and will generally range from about 0.001 fmol to 10 fmol, usually from about 0.005 fmol to 5 fmol and more usually from about 0.01 fmol to 1 fmol. Where the spot is made up of two or more distinct oligonucleotides of differing sequence, the molar ratio or copy number ratio of different oligonucleotides within each spot may be about equal or may be different, wherein when the ratio of unique oligonucleotides within each spot differs, the magnitude of the difference will usually be at least 2 to 5 fold but will generally not exceed about 10 fold. Where the spot has an overall circular dimension, the diameter of the spot will generally range from about 10 to 5,000 µm, usually from about 20 to 1,000 µm and more usually from about 50 to 500 µm. The surface area of each spot is at least about 100 µm², usually at least about 200 µm² and more usually at least about 400 µm², and may be as great as 25 mm² or greater, but will generally not exceed about 5 mm², and usually will not exceed about 1 mm².

Array Features

The arrays of the subject invention are characterized by having a plurality of probe spots as described above stably associated with the surface of a solid support. The density of probe spots on the array, as well as the overall density of probe and non-probe nucleic acid spots (where the latter are described in greater detail infra) may vary greatly. As used herein, the term nucleic acid spot refers to any spot on the array surface that is made up of nucleic acids, and as such includes both probe nucleic acid spots and non-probe nucleic acid spots. The density of the nucleic acid spots on the solid surface is at least about 5/cm² and usually at least about 10/cm² and may be as high as 1000/cm² or higher, but in many embodiments does not exceed about 1000/cm², and in these embodiments usually does not exceed about 500/cm² or 400/cm², and in certain embodiments does not exceed about 300/cm². The spots may be arranged in a spatially defined and physically addressable manner, in any convenient pattern across or over the surface of the array, such as in rows and columns so as to form a grid, in a circular pattern, and the like, where generally the pattern of spots will be present in the form of a grid across the surface of the solid support.

In the subject arrays, the spots of the pattern are stably associated with the surface of a solid support, where the support may be a flexible or rigid support. By "stably associated" it is meant that the oligonucleotides of the spots maintain their position relative to the solid support under hybridization and washing conditions. As such, the oligonucleotide members which make up the spots can be non-covalently or covalently stably associated with the support surface based on technologies well known to those of skill in the art. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between the spot oligonucleotides and a functional group present on the surface of the rigid support, e.g. —OH, where the functional group may be naturally occurring or present as a member of an introduced linking group. In many preferred embodiments, the nucleic acids making up the spots on the array surface, or at least the long oligonucleotides of the probe spots, are covalently bound to the support surface, e.g. through covalent linkages formed between moieties present on the probes (e.g. thymidine bases) and the substrate surface, etc.

As mentioned above, the array is present on either a flexible or rigid substrate. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible. As such, the rigid substrates of the subject arrays are sufficient to provide physical support and structure to the polymeric targets present thereon under the assay conditions in which the array is employed, particularly under high throughput handling conditions. Furthermore, when the rigid supports of the subject invention are bent, they are prone to breakage.

The solid supports upon which the subject patterns of spots are presented in the subject arrays may take a variety of configurations ranging from simple to complex, depending on the intended use of the array. Thus, the substrate could have an overall slide or plate configuration, such as a rectangular or disc configuration. In many embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.1 mm to 2 mm and more usually from about 0.2 to 1 mm. Thus, in one representative embodiment the support may have a micro-titre plate format, having dimensions of approximately 125×85 mm. In another representative embodiment, the support may be a standard microscope slide with dimensions of from about 25×75 mm.

The substrates of the subject arrays may be fabricated from a variety of materials. The materials from which the substrate is fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, is of particular interest in this embodiment. For rigid substrates, specific materials of interest include: glass; plastics, e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g. nylon or nitrocellulose, etc.

The substrates of the subject arrays comprise at least one surface on which the pattern of spots is present, where the surface may be smooth or substantially planar, or have irregularities, such as depressions or elevations. The surface on which the pattern of spots is present may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, polyacrylamides, and the like, where the polymers may be hetero- or homopolymeric, and may or may not have separate functional moieties attached thereto, e.g. conjugated.

The total number of spots on the substrate will vary depending on the number of different oligonucleotide probe spots (oligonucleotide probe compositions) one wishes to display on the surface, as well as the number of non probe spots, e.g control spots, orientation spots, calibrating spots and the like, as may be desired depending on the particular application in which the subject arrays are to be employed. Generally, the pattern present on the surface of the array will comprise at least about 10 distinct nucleic acid spots, usually at least about 20 nucleic acid spots, and more usually at least about 50 nucleic acid spots, where the number of nucleic acid spots may be as high as 10,000 or higher, but will usually not exceed about 5,000 nucleic acid spots, and more usually will not exceed about 3,000 nucleic acid spots and in many instances will not exceed about 2,000 nucleic acid spots. In certain embodiments, it is preferable to have each distinct probe spot or probe composition be presented in duplicate, i.e. so that there are two duplicate probe spots displayed on the array for a given target. In certain embodiments, each target represented on the array surface is only represented by a single type of oligonucleotide probe. In other words, all of the oligonucleotide probes on the array for a give target represented thereon have the same sequence. In certain embodiments, the number of spots will range from about 200 to 1200. The number of probe spots present in the array will typically make up a substantial proportion of the total number of nucleic acid spots on the array, where in many embodiments the number of probe spots is at least about 50 number %, usually at least about 80 number % and more usually at least about 90 number % of the total number of nucleic acid spots on the array. As such, in many embodiments the total number of probe spots on the array ranges from about 50 to 20,000, usually from about 100 to 10,000 and more usually from about 200 to 5,000.

In the arrays of the subject invention (particularly those designed for use in high throughput applications, such as high throughput analysis applications), a single pattern of oligonucleotide spots may be present on the array or the array may comprise a plurality of different oligonucleotide spot patterns, each pattern being as defined above. When a plurality of different oligonucleotide spot patterns are present, the patterns may be identical to each other, such that the array comprises two or more identical oligonucleotide spot patterns on its surface, or the oligonucleotide spot patterns may be different, e.g. in arrays that have two or more different types of target nucleic acids represented on their surface, e.g an array that has a pattern of spots corresponding to human genes and a pattern of spots corresponding to mouse genes. Where a plurality of spot patterns are present on the array, the number of different spot patterns is at least 2, usually at least 6, more usually at least 24 or 96, where the number of different patterns will generally not exceed about 384.

Where the array comprises a plurality of oligonucleotide spot patterns on its surface, preferably the array comprises a plurality of reaction chambers, wherein each chamber has a bottom surface having associated therewith an pattern of oligonucleotide spots and at least one wall, usually a plurality of walls surrounding the bottom surface. See e.g. U.S. Pat. No. 5,545,531, the disclosure of which is herein incorporated by reference. Of particular interest in many embodiments are arrays in which the same pattern of spots in reproduced in 24 or 96 different reaction chambers across the surface of the array.

Within any given pattern of spots on the array, there may be a single spot that corresponds to a given target or a number of different spots that correspond to the same target, where when a plurality of different spots are present that correspond to the same target, the probe compositions of each spot that corresponds to the same target may be identical or different. In other words, a plurality of different targets are represented in the pattern of spots, where each target may correspond to a single spot or a plurality of spots, where the oligonucleotide probe composition among the plurality of spots corresponding to the same target may be the same or different. Where a plurality of spots (of the same or different composition) corresponding to the same target is present on the array, the number of spots in this plurality will be at least about 2 and may be as high as 10, but will usually not exceed about 5. As mentioned above, however, in many preferred embodiments, however, any given target nucleic acid is represented by only a single type of probe spot, which may be present only once or multiple times on the array surface, e.g. in duplicate, triplicate etc.

The number of different targets represented on the array is at least about 2, usually at least about 10 and more usually at least about 20, where in many embodiments the number of different targets, e.g. genes, represented on the array is at least about 50 and more usually at least about 100. The number of different targets represented on the array may be as high as 5,000 or higher, but in many embodiments will usually not exceed about 3,000 and more usually will not exceed about 2,500. A target is considered to be represented on an array if it is able to hybridize to one or more probe compositions on the array.

Another feature of the present invention is that the relative binding efficiencies of each of the distinct long oligonucleotide probes for their respective targets is substantially the same, such that the binding efficiency of any two different long oligonucleotide probes on the arrays for their respective targets does not vary by more than about 20 fold, usually by not more than about 15 fold and more usually by not more than about 10 fold, where in many embodiments the binding efficiencies do not vary by more than about 5 fold and preferably by not more than about 3 fold.

In certain preferred embodiments of the invention, each of the probe spots in the array comprising the long oligonucleotide probe compositions correspond to the same kind of gene; i.e. genes that all share some common characteristic or can be grouped together based on some common feature, such as species of origin, tissue or cell of origin, functional role, disease association, etc. In this embodiment, each of the different target nucleic acids that corresponds to the different probe spots on the array are of the same type, i.e. that are coding sequences of the same type of gene. As such, the arrays of this embodiment of the subject invention will be of a specific array type. A variety of specific array types are provided by the subject invention. Specific array types of interest include: human, cancer, apoptosis, cardiovascular, cell cycle, hematology, mouse, human stress, mouse stress, oncogene and tumor suppressor, cell-cell interaction, cytokine and cytokine receptor, rat, rat stress, blood, mouse stress, neurobiology, and the like. For a more detailed description of the different target nucleic acids represented on at least some of these types of arrays, see PCT/US98/10561 the disclosure of which is herein incorporated by reference, as well as: U.S. patent application Ser. No. 08/859,998; U.S. patent application Ser. No. 08/974,298; U.S. patent application Ser. No. 09/225,998; U.S. application Ser. No. 09/221,480; U.S. application Ser. No. 09/222,432; U.S. application Ser. No. 09/222,436; U.S. application Ser. No. 09/222,437; U.S. application Ser. No. 09/222,251; U.S. application Ser. No. 09/221,481; U.S. application Ser. No. 09/222,256; U.S. application Ser. No. 09/222,248; and U.S. application Ser. No. 09/222,253; U.S. application Ser. No. 09/442,589 (entitled "Human Cardiovascular Array,"); U.S. application Ser. No. 09/440,302 (entitled "Human Neurobiology Array,"); U.S. application Ser. No. 09/454,226 (entitled "Rat Array,"); U.S. application Ser. No. 09/221,481 (entitled "Human Array,"); U.S. application Ser. No. 09/442,385 (entitled "Cancer Array,"); U.S. application Ser. No. 09/442,384 (entitled "Hematology/Immunology Array,"); U.S. application Ser. No. 09/441,920 (entitled "Mouse Stress/Toxicology Array,"); and U.S. application Ser. No. 09/440,305 (entitled "Rat Stress/Toxicology Array,"); the disclosures of which are incorporated herein by reference. In many embodiments, at least 20 different, usually at least 30 different and often at least 50 different genes and in many embodiments at least 100 of different genes from the tables of genes listed in these applications are represented on the subject arrays.

With respect to the oligonucleotide probes that correspond to a particular type or kind of gene, type or kind can refer to a plurality of different characterizing features, where such features include: species specific genes, where specific species of interest include eukaryotic species, such as mice, rats, rabbits, pigs, primates, humans, etc.; function specific genes, where such genes include oncogenes, apoptosis genes, cytokines, receptors, protein kinases, etc.; genes specific for or involved in a particular biological process, such as apoptosis, differentiation, stress response, aging, proliferation, etc.; cellular mechanism genes, e.g. cell-cycle, signal transduction, metabolism of toxic compounds, etc.; disease associated genes, e.g. genes involved in cancer, schizophrenia, diabetes, high blood pressure, atherosclerosis, viral-host interaction and infection diseases, etc.; location specific genes, where locations include organ, such as heart, liver, prostate, lung etc., tissue, such as nerve, muscle, connective, etc., cellular, such as axonal, lymphocytic, etc, or subcellular locations, e.g. nucleus, endoplasmic reticulum, Golgi complex, endosome, lysosome, peroxisome, mitochondria, cytoplasm, cytoskeleton, plasma membrane, extracellular space, chromosome-specific genes; specific genes that change expression level over time, e.g. genes that are expressed at different levels during the progression of a disease condition, such as prostate genes which are induced or repressed during the progression of prostate cancer.

In addition to the oligonucleotide spots comprising the oligonucleotide probe compositions (i.e. oligonucleotide probe spots), the subject arrays may comprise one or more additional spots of polynucleotides or nucleic acid spots which do not correspond to target nucleic acids as defined above, such as target nucleic acids of the type or kind of gene represented on the array in those embodiments in which the array is of a specific type. In other words, the array may comprise one or more non probe nucleic acid spots that are made of non "unique" oligonucleotides or polynucleotides, i.e common oligonucleotides or polynucleotides. For example, spots comprising genomic DNA may be provided in the array, where such spots may serve as orientation marks. Spots comprising plasmid and bacteriophage genes, genes from the same or another species which are not expressed and do not cross hybridize with the cDNA target, and the like, may be present and serve as negative controls. In addition, spots comprising a plurality of oligonucleotides complimentary to housekeeping genes and other control genes from the same or another species may be present, which spots serve in the normalization of mRNA abundance and standardization of hybridization signal intensity in the sample assayed with the array. Orientation spots may also be included on the array, where such spots serve to simplify image analysis of hybrid patterns. Other types of spots include spots for calibration or quantitative standards, controls for integrity of RNA template (targets), controls for efficiency steps in target preparation (such as efficiency of labeling, purification and hybridization), etc. These latter types of spots are distinguished from the oligonucleotide probe spots, i.e. they are non-probe spots.

Array Preparation

The subject arrays can be prepared using any convenient means. One means of preparing the subject arrays is to first synthesize the oligonucleotides for each spot and then deposit the oligonucleotides as a spot on the support surface. The oligonucleotides may be prepared using any convenient methodology, where chemical synthesis procedures using phorphoramidite or analogous protocols in which individual bases are added sequentially without the use of a polymerase, e.g. such as is found in automated solid phase synthesis protocols, and the like, are of particular interest, where such techniques are well known to those of skill in the art.

In determining the specific oligonucleotides of the probe compositions, the oligonucleotide should be chosen so that is capable of hybridizing to a region of the target nucleic acid or gene having a sequence unique to that gene. Different methods may be employed to choose the specific region of the gene to which the oligonucleotide probe is to hybridize. Thus, one can use a random approach based on availability of a gene of interest. However, instead of using a random approach which is based on availability of a gene of interest, a rational design approach may also be employed to choose the optimal sequence for the hybridization array. Preferably, the region of the gene that is selected in preparing the oligonucleotide probe is chosen based on the following criteria. First, the sequence that is chosen as the target specific sequence should yield an oligonucleotide probe that does not cross-hybridize with, or is homologous to, any other oligonucleotide probe for other spots present on the array that do not correspond to the target gene. Second, the sequence should be chosen such that the oligonucleotide probe has a low homology to a nucleotide sequence found in any other gene, whether or not the gene is to be represented on the array from the same species of origin. As such, sequences that are avoided include those found in: highly expressed gene products, structural RNAs, repeated sequences found in the RNA sample to be tested with the array and sequences found in vectors. A further consideration is to select sequences which provide for minimal or no secondary structure, structure which allows for optimal hybridization but low non-specific binding, equal or similar thermal stabilities, and optimal hybridization characteristics. A final consideration is to select probe sequences that give rise to probes which efficiently hybridize to their corresponding target and do not suffer from substantial non-specific hybridization events. Finally, all of the probe sequences on the array are preferably chosen such that they exhibit substantially the same hybridization efficiency to their corresponding probes, where the difference in hybridization efficiency between any two probes and their corresponding targets preferably does not exceed about 10 fold, more preferably does not exceed about 5 fold and most preferably does not exceed about 3 fold.

Probes meeting the above criteria can be designed or identified using any convenient protocol. A representative protocol includes the following algorithm which is part of the present invention. In selecting probes according to this representative algorithm or process, a unique gene-specific or target specific sequence (one or more regions per gene) is first identified based on a sequence homology search algorithm described in detail in copending application Ser. No. 09/053, 375, the disclosure of which is herein incorporated by reference. In this step, the sequence of all genes represented on the to be produced array and all sequences deposited in GenBank are searched in order to select mRNA fragments which are unique for each mRNA or target to be represented on the array. A unique sequence is defined as a sequence which at least does not have significant homology to any other sequence on the array. For example, where one is interested in identifying suitable 80 base long unique probes, sequences which do not have homology of more than about 80% to any consecutive 40 base segment of any of the other probes on the array are selected. This step typically results in a reduced population of candidate probe sequences as compared to the initial population of possible sequences identified for each specific target.

Of this reduced population of candidate sequences, screening criteria are employed to exclude non-optimal sequences, where sequences that are excluded or screened out in this step include: (a) those with strong secondary structure or self-complementarity (for example long hairpins); (b) those with very high (more than 70%) or very low (less than 40%) GC content; (c) those with long stretches (more than 6) of identical consecutive bases or long stretches of sequences enriched in some motifs, purine or pyrimidine stretches or particular bases, like GAGAGAGA . . . , GAAGAGAA; and the like. This step results in a further reduction in the population of candidate probe sequences.

In the next step, sequences are selected that have similar melting temperatures or thermodynamic stability which will provide similar performance in hybridization assays with target nucleic acids. Of interest is the identification of probes that can participate in duplexes whose melting temperature exceeds 65, usually at least about 75 and more usually at least about 80° C.

The final step in this representative design process is to select from the remaining sequences those sequences which provide for low levels of non-specific hybridization and similar high efficiency hybridization with complementary target molecules. This final selection is accomplished by practicing the following steps:

1. The remaining set of probes which is identified for each target using the above steps, where this remaining set typically includes at least 1 potential probe, usually at least 2 potential probes and more usually at least 3 potential probes, are experimentally characterized for their hybridization efficiency and propensity to participate in non-specific hybridization events using the following protocol.
2. First, an array of at least a portion of the candidate probes for each target to be represented on the final array is produced. For example, where three candidate probes have been identified for a particular target sequence, these probes are attached to the surface of a solid support, along with candidate probes for other targets, to produce a test probe array.
3. Next, a normalization control target set is prepared, wherein each target in the set is complementary to one probe sequence in the array and the various target constituents of the set are mixed in similar or identical amounts. The number of targets in the set of control targets is usually less than the set of probes in the array. Usually the number of targets in the control set is between 50% and 90%, but can be between 10 and 100%, of the number of test probes on the array surface. As such, not all of the probe sequences on the test array will have a corresponding or complementary target in the target control set. For example, where three different candidate probes have been identified for each of 10 different mRNA targets, a test probe array of 30 different oligonucleotide probes is prepared. Next, a control set of target nucleic acids which includes targets that correspond to 5 of the 10 different mRNA targets represented on the array is produced, where the control set includes a target that is complementary to each different probe corresponding to 1 of the 5 different mRNAs represented in the control target set, i.e. the control target set includes 15 different targets—1 target for each of the 15 probes on the array that correspond to the 5 different mRNAs represented in the control target set. (While the above procedure has been described in terms of using a target population that corresponds to less than all of the probes on the array so that non-specific hybridization can be determined, other protocols also may be employed. For example, one may use a population of targets that corresponds to all of the probes on the array, where at least a portion of the targets are distinguishable from the remaining portion or portions, e.g. by label, mass etc. Following hybridization, the targets hybridized to each probe can be detected and both the efficiency of the probe for its true target and its propensity for non-specific hybridization can be determined).

4. Following generation of the control set of targets, the control set is hybridized with the test probe array under stringent conditions and hybridization signals are detected. The intensity of the signal for those probes which have a corresponding labeled complementary target in the hybridization solution is used as a measure for determining the hybridization efficiency of that probe, as well as differences in hybridization efficiency of different candidate probes for different targets. For those probes on the array which do not have complementary labeled target sequences in control set, the intensity of hybridization s these probes is used to identify the level of non-specific characterizes these probes.

5. The above steps are repeated with one or more additional control sets of target nucleic acids in order to get comprehensive information concerning the hybridization efficiency and level of non-specific hybridization for each candidate of the candidate probes on the array. The number of different sets of control targets that are employed in this process is generally at least two, more commonly at least four and most commonly at least ten.

6. From the above steps, probe sequences meeting the following criteria are identified for use as long oligonucleotide probes in the arrays of the subject invention. First, candidate probes that exhibit a high efficiency of hybridization for their corresponding targets are identified. In many embodiments, candidate probes having substantially the same hybridization efficiency for the respective targets are identified, where any two probes to different targets have substantially the same hybridization efficiency for their respective targets if the differences in hybridization efficiency of the two probes does not exceed 10-fold, where differences of less than about 5-fold and often less than about 3-fold are preferred. Of these identified probes, probes that show substantial cross hybridization or non-specific hybridization are excluded, where a probe that shows non-specific hybridization of up to at least 5-fold, more commonly 20-fold and most commonly 50-fold less than the level of gene-specific hybridization between the probe and its corresponding target are excluded in this step. In other words, in the above assay hybridizations, those probes that exhibit a signal that is at within 5-fold less, usually at least 20-fold less and more usually within 50-fold less of the signal generated by probes and their complementary targets are excluded as being probes with unacceptably high propensities for participating in non-specific hybridization events.

The above algorithm or process is used to design the long oligonucleotide probes that are present on the arrays of the subject invention. Steps 1 to 6 can be repeated if, in the first round of selection for particular targets no array candidate probes were identified. Once the design or sequence of the probes is identified, the long oligonucleotide probes may be synthesized according to any convenient protocol, as mentioned above, e.g. via phosphoramidite processes.

Following synthesis of the subject long oligonucleotide probes, the probes are stably associated with the surface of the solid support. This portion of the preparation process typically involves deposition the probes, e.g. a solution of the probes, onto the surface of the substrate, where the deposition process may or may not be coupled with a covalent attachment step, depending on how the probes are to be stably attached to the substrate surface, e.g. via electrostatic interactions, covalent bonds, etc. The prepared oligonucleotides may be spotted on the support using any convenient methodology, including manual techniques, e.g. by micro pipette, ink jet, pins, etc., and automated protocols. Of particular interest is the use of an automated spotting device, such as the Bio-Grid Arrayer (Biorobotics).

Where desired, the long oligonucleotides can be covalently bonded to the substrate surface using a number of different protocols. For example, functionally active groups such as amino, etc., can be introduced onto the 5' or 3' ends of the oligonucleotides, where the introduced functionalities are then reacted with active surface groups on the substrate to provide the covalent linkage. In certain preferred embodiments, the long oligonucleotide probes are covalently bonded to the surface of the substrate using the following protocol. In this process, the probes are covalently attached to the substrate surface under denaturing conditions. Typically, a denaturing composition of each probe is prepared and then deposited on the substrate surface. By denaturing composition is meant that the probe molecules present in the composition are not participating in secondary structures, e.g. through self-hybridization or hybridization to other molecules in the composition. The denaturing composition, typically a fluid composition, may be any composition which inhibits the formation of hydrogen bonds between complementary nucleotide bases. Thus, compositions of interest are those that include a denaturing agent, e.g. urea, formamide, sodium thiocyanate, etc., as well as solutions having a high pH, e.g. 12 to 13.5, usually 12.5 to 13, or a low pH, e.g. 1 to 4, usually 1 to 3; and the like. In many preferred embodiments, the composition is a strongly alkaline solution of the long oligonucleotide, where the composition comprises a base, e.g. sodium hydroxide, lithium hydroxide, potassium hydroxide, ammonium hydroxide, tetramethyl ammonium hydroxide, ammonium hydroxide, etc, in sufficient amounts to impart the desired high pH to the composition, e.g. 12.5 to 13.0. The concentration of long oligonucleotide in the composition typically ranges from about 0.1 to 10 µM, usually from about 0.5 to 5 µM. Following deposition of the denaturing composition of the long oligonucleoide probe onto the substrate surface, the deposited probe is exposed to UV radiation of sufficient wavelength, e.g. from 250 to 350 nm, to cross link the deposited probe to the surface of the substrate. The irradiation wavelength for this process typically ranges from about 50 to 1000 mJoules, usually from about 100 to 500 mJoules, where the duration of the exposure typically lasts from about 20 to 600 sec, usually from about 30 to 120 sec.

The above protocol for covalent attachment results in the random covalent binding of the long oligonucleotide probe to the substrate surface by one or more attachment sites on the probe, where such attachment may optionally be enhanced through inclusion of oligodT regions at one or more ends of the oligonucleotides, as discussed supra. An important feature of the above process is that reactive moieties, e.g. amino, that are not present on naturally occurring oligonucleotides are not employed in the subject methods. As such, the subject methods are suitable for use with oligonucleotides that do not include moieties that are not present on naturally occurring nucleic acids.

The above described covalent attachment protocol may be used with a variety of different types of substrates. Thus, the above described protocols can be employed with solid supports, such as glass, plastics, membranes, e.g. nylon, and the like. The surfaces may or may not be modified. For example, the nylon surface may be charge neutral or positively charged, where such substrates are available from a number of commercial sources. For glass surfaces, in many embodiments the glass surface is modified, e.g. to display reactive functionalities, such as amino, phenyl isothiocyanate, etc.

Methods of Using the Subject Arrays

The subject arrays find use in a variety of different applications in which one is interested in detecting the occurrence of one or more binding events between target nucleic acids and probes on the array and then relating the occurrence of the binding event(s) to the presence of a target(s) in a sample. In general, the device will be contacted with the sample suspected of containing the target under conditions sufficient for binding of any target present in the sample to complementary oligonucleotides present on the array. Generally, the sample will be a fluid sample and contact will be achieved by introduction of an appropriate volume of the fluid sample onto the array surface, where introduction can be through delivery ports, direct contact, deposition, and the like.

Generation of Labeled Target

Targets may be generated by methods known in the art. mRNA can be labeled and used directly as a target, or converted to a labeled cDNA target. Alternatively, an excess of synthetic labeled oligonucleotide target which is complementary to the probes on the array can be hybridized with the mRNA, followed by separation of any unbound target from the hybridized fraction or isolation of the hybridized fraction. The hybridized fraction can then hybridized to the array to reveal the expression pattern of the cellular source from which the mRNA was derived. Usually, mRNA is labeled non-specifically (randomly) directly using chemically, photochemically or enzymatically activated labeling compounds, such as photobiotin (Clontech, Palo Alto, Calif.), Dig-Chem-Link (Boehringer), and the like. In another way, mRNA target can be labeled specifically in the sequences which are complementary to the probes. This specific labeling can be achieved by using covalent or non-covalent binding of additional labeled oligonucleotides (or mimetics) to the target sequences which flank the probe complementary sequence or the complementary probe sequence. The hybridized fraction of labeled oligonucleotides with mRNA can be purified or separated from the non-hybridized fraction and then hybridized to the array. Generally, methods for generating labeled cDNA probes include the use of oligonucleotide primers. Primers that may be employed include oligo dT, random primers, e.g. random hexamers and gene specific primers, as described in PCT/US98/10561, the disclosure of which is herein incorporated by reference.

Where gene specific primers are employed, the gene specific primers are preferably those primers that correspond to the different oligonucleotide spots on the array. Thus, one will preferably employ gene specific primers for each different oligonucleotide that is present on the array, so that if the gene is expressed in the particular cell or tissue being analyzed, labeled target will be generated from the sample for that gene. In this manner, if a particular gene present on the array is expressed in a particular sample, the appropriate target will be generated and subsequently identified. For each target represented on the array, a single gene specific primer may be employed or a plurality of different gene specific primers may be employed, where when a plurality are used to produce the target, the number will generally not exceed about 3. Generally, in preparing the target from template nucleic acid, e.g. mRNA, the gene specific primers will hybridize to a region of the template that is downstream from the region to which the probes are homologous, e.g. to which the probes are complementary or have the same sequence. The distance from oligonucleotide probe sequence and primer binding site generally does not exceed about 500 nt, usually does not exceed about 300 nt and more usually does not exceed about 200 nt. However, in certain embodiments the gene specific primers may be partially or completely complementary to the oligonucleotide probes. The cDNA probe can be further amplified by PCR or can be converted (linearly amplified) using phage coded RNA polymerase transcription of dsDNA. See PCT/US98/1056, the disclosure of which is herein incorporated by reference.

In many embodiments, the target that is generated in this step is a linear target which is devoid of any secondary structure, e.g. as produced by target intramolecular interactions such as hydrogen bonds. However, in certain embodiments, it may be desirable to generate a conformationally restricted to constrained target, e.g. a target that forms a hairpin loop structure under the hybridization conditions in which the target is employed. One means of producing hairpin loop targets is to employ primers that include an anchoring sequence in addition to priming sequence in the enzymatic target generation step. The anchoring domain of the primer, which is 5' of the priming domain, is a domain that is complementary to a region of the first strand cDNA distal to the 5' end that is generated during target synthesis, where the 5' distal region to which the anchor is complementary is sufficiently separated from the 5' end of the cDNA such that the cDNA forms a hairpin loop structure in which the anchor sequence of the 5' distal region to which the anchor sequence is complementary form the stem structure. The sequence of the anchor domain of the primer is typically chosen to provide for a loop that ranges in size from about 20 to 200 nt, usually from about 30 to 100 nt and more usually from about 40 to 80 nt. The primers used to generate these hairpin loop targets are described by the following formula:

wherein

N is dGMP, dCMP, dAMP and dTMP;

p is an integer ranging from 12 to 35, usually from 15 to 30 and more usually from 18 to 25, such that Np is the priming domain of the primer, and may be a gene specific domain, as described above, or an oligo dT domain; and x is an integer ranging from 3 to 30, usually from 5 to 20 and more usually from 5 to 15, wherein Nx is the anchor domain and is complementary to a 5' distal portion of the first strand cDNA that is complementary to the mRNA of interest which is to be represented as target.

A variety of different protocols may be used to generate the labeled target nucleic acids, as is known in the art, where such methods typically rely in the enzymatic generation of the labeled target using the initial primer. Labeled primers can be employed to generate the labeled target. Alternatively, label can be incorporated during first strand synthesis or subsequent synthesis labeling or amplification steps, including chemical or enzymatic labeling steps, in order to produce labeled target. Representative methods of producing labeled target are disclosed in PCT/US98/10561, the disclosure of which is herein incorporated by reference.

Hybridization and Detection

As mentioned above, following preparation of the target nucleic acid from the tissue or cell of interest, the target nucleic acid is then contacted with the array under hybridization conditions, where such conditions can be adjusted, as desired, to provide for an optimum level of specificity in view of the particular assay being performed. Suitable hybridization conditions are well known to those of skill in the art and reviewed in Maniatis et al, supra and WO 95/21944. Of particular interest in many embodiments is the use of stringent conditions during hybridization, i.e. conditions that are optimal in terms of rate, yield and stability for specific probe-target hybridization and provide for a minimum of non-specific probe/target interaction. Stringent conditions are known to those of skill in the art. In the present invention, stringent conditions are typically characterized by temperatures ranging from 15 to 35, usually 20 to 30° C. less than the melting temperature of the probe target duplexes, which melting temperature is dependent on a number of parameters, e.g. temperature, buffer compositions, size of probes and targets, concentration of probes and targets, etc. As such, the temperature of hybridization typically ranges from about 55 to 70, usually from about 60 to 68° C. In the presence of denaturing agents, the temperature may range from about 35 to 45, usually from about 37 to 42° C. The stringent hybridization conditions are further typically characterized by the presence of a hybridization buffer, where the buffer is characterized by one or more of the following characteristics: (a) having a high salt concentration, e.g. 3 to 6×SSC (or other salts with similar concentrations); (b) the presence of detergents, like SDS (from 0.1 to 20%), triton X100 (from 0.01 to 1%), monidet NP40 (from 0.1 to 5%) etc.; (c) other additives, like EDTA (typically from 0.1 to 1 μM), tetramethylammonium chloride; (d) accelerating agents, e.g. PEG, dextran sulfate (5 to 10%), CTAB, SDS and the like; (e) denaturing agents, e.g. formamide, urea etc.; and the like.

In analyzing the differences in the population of labeled target nucleic acids generated from two or more physiological sources using the arrays described above, in certain embodiments each population of labeled target nucleic acids are separately contacted to identical probe arrays or together to the same array under conditions of hybridization, preferably under stringent hybridization conditions, such that labeled target nucleic acids hybridize to complementary probes on the substrate surface. In yet other embodiments, labeled target nucleic acids are combined with a distinguishably labeled standard or control target nucleic acids followed by hybridization of the combined populations to the array surface, as described in application Ser. No. 09/298,361; the disclosure of which is herein incorporated by reference.

Where all of the target sequences comprise the same label, different arrays will be employed for each physiological source (where different could include using the same array at different times). Alternatively, where the labels of the targets are different and distinguishable for each of the different physiological sources being assayed, the opportunity arises to use the same array at the same time for each of the different target populations. Examples of distinguishable labels are well known in the art and include: two or more different emission wavelength fluorescent dyes, like Cy3 and Cy5, two or more isotopes with different energy of emission, like $^{32}$P and $^{33}$P, gold or silver particles with different scattering spectra, labels which generate signals under different treatment conditions, like temperature, pH, treatment by additional chemical agents, etc., or generate signals at different time points after treatment. Using one or more enzymes for signal generation allows for the use of an even greater variety of distinguishable labels, based on different substrate specificity of enzymes (alkaline phosphatase/peroxidase).

Following hybridization, non-hybridized labeled nucleic acid is removed from the support surface, conveniently by washing, generating a pattern of hybridized nucleic acid on the substrate surface. A variety of wash solutions are known to those of skill in the art and may be used.

The resultant hybridization patterns of labeled nucleic acids may be visualized or detected in a variety of ways, with the particular manner of detection being chosen based on the particular label of the target nucleic acid, where representative detection means include scintillation counting, autoradiography, fluorescence measurement, calorimetric measurement, light emission measurement, light scattering, and the like.

Following detection or visualization, the hybridization patterns may be compared to identify differences between the patterns. Where arrays in which each of the different probes corresponds to a known gene are employed, any discrepancies can be related to a differential expression of a particular gene in the physiological sources being compared.

The provision of appropriate controls on the arrays permits a more detailed analysis that controls for variations in hybridization conditions, cross-hybridization, non-specific binding and the like. Thus, for example, in a preferred embodiment, the hybridization array is provided with normalization controls as described supra. These normalization controls are probes complementary to control target sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Normalization control is also useful to adjust (e.g. correct) for differences which arise from the array quality, the mRNA sample quality, efficiency of first-strand synthesis, etc. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes. The resulting values may be multiplied by a constant value to scale the results.

In certain embodiments, normalization controls are often unnecessary for useful quantification of a hybridization signal. Thus, where optimal probes have been identified, the average hybridization signal produced by the selected optimal probes provides a good quantified measure of the concentration of hybridized nucleic acid. However, normalization controls may still be employed in such methods for other purposes, e.g. to account for array quality, mRNA sample quality, etc.

Utility

The subject methods find use in, among other applications, differential gene expression assays. Thus, one may use the subject methods in the differential expression analysis of: (a) diseased and normal tissue, e.g. neoplastic and normal tissue, (b) different tissue or tissue types; (c) developmental stage; (d) response to external or internal stimulus; (e) response to treatment; and the like. The subject arrays therefore find use in broad scale expression screening for drug discovery, diagnostics and research, as well as studying the effect of a particular active agent on the expression pattern of genes in a particular cell, where such information can be used to reveal drug toxicity, carcinogenicity, etc., environmental monitoring, disease research and the like.

Kits

Also provided are kits for performing analyte binding assays using the subject devices, where kits for carrying out differential gene expression analysis assays are preferred. Such kits according to the subject invention will at least comprise the subject arrays. The kits may further comprise one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The following examples are offered by way of illustration and not by way of limitation.

EXPERIMENTAL

In the following examples, all percentages are by weight and all solvent mixture proportions are by volume unless otherwise noted.

Example 1

Generation of $^{32}$P-Labeled Hybridization Target

Step A. cDNA Synthesis/Labeling Procedure

The 10-μl reaction described below convert 1 μg of synthetic control RNA into $^{32}$P labeled first-strand cDNA.

For each labeling reaction:
1. Prepare enough master mix for all labeling reactions and 1 extra reaction to ensure sufficient volume. For each 10-μl labeling reaction, mix the following reagents:
   2 μl 5× First-strand buffer (250 μM Tris-HCl pH8.3; 375 mM KCl; 15 mM MgCl$_2$)
   1 μl 10× dNTP mix (500 μM dGTP, 500 μM dCTP, 500 μM dTTP, 5 μM DATP)
   4 μl [α-$^{33}$P]dATP (Amersham, 2500 Ci/mmol, 10 mCi/ml)
   1 μl MMLV reverse transcriptase (Amersham, 200 units/μl)
   8 μl Final volume
2. Combine the following in a 0.5-ml PCR test tube:
   1 μg (1 μl) control s64 RNA
   1 μl gene-specific primer s64 (0.2 μM)

```
CGGCCAGGATACCAAAGCCTTACAG    (SEQ ID NO:02)
```

The control s64 RNA provided above was synthesized by T7 transcription from cDNA fragment corresponding to the human DNA repair protein XRCC9 (GB accession number U70310) as described in more details in patent application Ser. No. 09/298,361, the disclosure of which is herein incorporated by reference.
3. Add ddH$_2$O to a final volume of 3 μl.
4. Mix contents and spin the tubes briefly in a microcentrifuge.
5. Incubate the tubes in preheated PCR thermocycler at 70° C. for 2 min.
6. Reduce temperature in thermocycle down to 50° C. and incubate for 2 min.
7. Add 8 μl of master mix to each reaction test tube.
8. Mix the contents of the test tubes by gentle pipetting.
9. Incubate the tubes in PCR thermocycler for 20 min at 50° C.
10. Stop the reaction by adding 1 μl of 10× termination mix (0.1 M EDTA, 1 mg/ml glycogen).

Step B. Column Chromatography

To purify the $^{32}$P-labeled cDNAs from unincorporated $^{32}$P-labeled nucleotides and small (<0.1-kb) cDNA fragments, follow this procedure for each test tube:
1. Remove CHROMA SPIN-200 column (CLONTECH) from refrigerator and warm up at room temperature for about 1 hour. Invert the column several times to completely re-suspend the gel matrix.

Note: Check for air bubbles in the column matrix. If bubbles are visible, re-suspend the matrix in the in the column buffer (ddH$_2$O) by inverting the column again.
2. Remove the bottom cap from the column, and then slowly remove the top cap.
3. Place the column into a 1.5-ml microcentrifuge tube.
4. Let the water drain through the column by gravity flow until you can see the surface of the gel beads in the column matrix. The top of the column matrix should be at 0.75-ml mark on the wall of the column. If the column contains less matrix, adjust the volume of the matrix to 0.75-ml mark using matrix from another column.
5. Discard the collected water and proceed with purification.
6. Carefully and slowly apply the sample to the center of the gel bed's flat surface and allow sample to be fully absorbed into the resin bed before proceeding to the next step. Do not allow any sample to flow along the inner wall of the column.
7. Apply 25 μl of ddH$_2$O and allow the water to completely drain out of the column.
8. Apply 200 μl of ddH$_2$O and allow the buffer to completely drain out of the column until there is no liquid left above the resin bed.
9. Transfer column to a clean 1.5-ml microcentrifuge tube.

```
    GGCCA GGATACCAAA GCCTTACAGG ACTTCCTCCT CAGTGTGCAG ATGTGCCCAG GTAATCGAGA  (SEQ ID NO:01)
CACTTACTTT CACCTGCTTC AGACTCTGAA GAGGCTAGAT CGGAGGGATG AGGCCACTGC
ACTCTGGTGG AGGCTGGAGG CCCAAACTAA GGGGTCACAT GAAGATGCTC TGTGGTCTCT
CCCCCTGTAC CTAGAAAGCT ATTTGAGCTG GATCCGTCCC TCTGATCGTG ACGCCTTCCT
TGAAGAATTT CGGACATCTC TGCCAAAGTC TTGTGACCTG TAGCTGCC
```

10. To collect the first fraction add 100 µl of ddH$_2$O to the column and allow the water to completely drain out of the column.
11. To collect the second, third and fourth fractions repeart steps 9-10.
12. Place the tubes with fractions 1-4 in a scintillation counter empty vials (do not add scintillation cocktail to the tubes or vials), and obtain Cerenkov counts for each fraction. Count the entire sample in the tritium channel.
13. Pool the fractions (usually fractions 2-3) which show the highest Cerenkov counts. Waist column and the fractions (usually fraction 1 and 4) which show less than 10% counts from peak fractions. Total incorporation into peak fractions should be 2-5×10$^6$ cpm.

Example 2

Preparation of Amynopropyl-Glass

1. Prepare wash solution: to get 2 liters, dissolve 200 g NaOH in 600 ml water and make up volume to 1 liter (20% w/v). To this solution add 1 liter ethanol. This makes 10% NaOH in 50% EtOH. Wash glass in this solution on orbital shaker overnight. (slides are placed in rack)
2. Transfer rack(s) with slides into bath with MilliQ water and wash on shaker for 15-20 min, repeat this step one more time.
3. Transfer slides into bath with acetone and wash on shaker for 15-20 min. Repeat this step two more times. Dispose acetone from first wash and keep acetone from 2$^{nd}$ and 3$^{rd}$ washes. (When doing this procedure again, use 2$^{nd}$ wash as first, 3$^{rd}$ as second and for the 3$^{rd}$ wash use fresh acetone.
4. Prepare in advance 5% solution of water in acetone (5% water-95% acetone).
5. During last wash step prepare 0.5% solution of aminopropyltriethoxysilane (Sigma, cat No A3648) in acetone-water mixture from step 4.
6. Transfer slides from last acetone wash into silanization solution and incubate for 2 hours at room temperature on orbital shaker.
7. Transfer slides into MilliQ water and wash for 20 minutes.
8. Transfer slides into acetone and wash for 20 min, repeat this step 2 more times. These acetone washes are to be disposed.
9. Preheat oven at 110° C.
10. Remove rack with slides from the last acetone wash and transfer it into preheated oven. As some acetone still remains on slides and on rack's surfaces, the smelt becomes quite intensive. Exhaust duct should be open after putting slides into oven and may be closed after first 30 minutes of baking.
11. Program oven to bake slides at 110° C. for 3 hours and then shut down or cool down to room temperature. It is convenient to do this step overnight.
12. After baking is oven, slides are ready for printing using "thiocyanate method". If the printing will not be done right away, slides may be kept in clean boxes inside dry cabinets.

The following steps are for preparation of PDITC-slides.
1. Prepare a mixture of Pyridine and Dimethylformamide (10% pyridine and 90% DMF). Prepare only as much as necessary. This mixture cannot be stored.
2. Dissolve 1,4-Phenylenediisothiocyanate in the Pyridine-DMF mixture at 0.1% concentration (1 g per liter) on stirrer. Prepare this solution only as much as necessary and only when ready to proceed with next steps. This solution cannot be stored. The solution should be light yellow-green in color.
3. Pour the solution in a tray and transfer tray(s) with amino-modified slides into the solution. Close the tray with the lid and shake on orbital shaker at low speed for 2 hours.
4. Transfer rack(s) with slides into a tray with acetone and wash on shaker for 10-15 minutes. Repeat this step 2 more times by transferring rack(s) into trays with fresh acetone.
5. After last wash quickly transfer racks with slides into vacuum oven and dry in vacuum at room temperature for 20-30 minutes. Vacuum should be applied as fast as possible.
6. Dispose Pyridine-DMF mixture and acetone washes into flammable wastes container.
7. Transfer slides for storage into dry cabinets. Make sure the desiccant in the dry cabinet is good (blue in color).

Example 3

Printing of Oligonucleotides

Oligonucleotides used in this experiment were dissolved in 0.1 M NaOH at 100 nanogramm per microliter and printed on PDITC modified glass surface. Amount of DNA deposited was about 5 ng per spot. After printing slides were baked at 80° C. for 2 hours and then UV crosslinked (254 nm UV lamp) for 1 min.

Example 4

Preparation of Array

Using the above protocol describe in Examples 5 & 6, an array having the characteristics of Table 1 was prepared. Each of the probe oligonucleotides was prepared using an automated nucleic acid synthesizer.

TABLE 1

| Array Position | Probe Name | Probe Sequence |
|---|---|---|
| A1 | s64_2 | AC CTAGAAAGCT ATTTGAGCTG GATCCGTCCC TCTGATCGTG ACGCCTTCCT TGAAGAATTT CGGACATCTC TGCCAAAGTC TTGTGACCTG TAGCTGCCA |
| A2 | s64_2_90 | AGAAAGCTATTTGAGCTGGATCCGTCCCTCTGATCGTGACGCCTTCCTTGAAGAATTTCGGACATCTCTGCCAAAGTCTTGTGACCTGTA |
| A3 | s64_2_80 | AGCTATTTGAGCTGGATCCGTCCCTCTGATCGTGACGCCTTCCTTGAAGAATTTCGGACATCTCTGCCAAAGTCTTGTGA |
| A4 | s64_2_70 | ATTTGAGCTGGATCCGTCCCTCTGATCGTGACGCCTTCCTTGAAGAATTTCGGACATCTCTGCCAAAGTA |
| B1 | s64_2_60 | AGCTGGATCCGTCCCTCTGATCGTGACGCCTTCCTTGAAGAATTTCGGACATCTCTGCCA |

TABLE 1-continued

| Array Position | Probe Name | Probe Sequence |
|---|---|---|
| B2 | s64_2_50 | AATCCGTCCCTCTGATCGTGACGCCTTCCTTGAAGAATTTCGGACATCTA |
| C1 | s26_2 | AAACCCAGGA AATACCAAA TCCAGATTTC TTTGAAGATC TGGAACCTTT CAGAATGACT CCTTTAGTG CTATTGGTTT GGAGCTGTGG TCCATGACCTA |
| C2 | s26_2_90 | AGGAAAATACCAAATCCAGATTTCTTTGAAGATCTGGAACCTTTCAGAATGACTCCTTTTAGTGCTATTGGTTTGGAGCTGTG GTCCATA |
| C3 | s26_2_80 | AATACCAAATCCAGATTTCTTTGAAGATCTGGAACCTTTCAGAATGACTCCTTTTAGTGCTATTGGTTTGGAGCTGTGGA |
| C4 | s26_2_70 | AAAATCCAGATTTCTTTGAAGATCTGGAACCTTTCAGAATGACTCCTTTTAGTGCTATTGGTTTGGAGCA |
| D1 | s26_2_60 | ACAGATTTCTTTGAAGATCTGGAACCTTTCAGAATGACTCCTTTTAGTGCTATTGGTTTA |
| D2 | s26_2_50 | ATTCTTTGAAGATCTGGAACCTTTCAGAATGACTCCTTTTAGTGCTATTA |
| A5 and E5 | c370_2 | AGGGTC AGCTGATCTA CGAGTCTGCC ATCACCTGTG AGTACCTGGA TGAAGCATAC CCAGGGAAGA AGCTGTTGCC GGATGACCCC TATGAGAAAG CTTGCA |
| A6 and E6 | c370_2_90 | AAGCTGATCTACGAGTCTGCCATCACCTGTGAGTACCTGGATGAAGCATACCCAGGGAAGAAGCTGTTGCCGGATGACCCCTA TGAGAAA |
| A7 and E7 | c370_2_80 | AATCTACGAGTCTGCCATCACCTGTGAGTACCTGGATGAAGCATACCCAGGGAAGAAGCTGTTGCCGGATGACCCCTATA |
| A8 and E8 | c370_2_70 | ACGAGTCTGCCATCACCTGTGAGTACCTGGATGAAGCATACCCAGGGAAGAAGCTGTTGCCGGATGACCA |
| B5 and F5 | c370_2_60 | ACTGCCATCACCTGTGAGTACCTGGATGAAGCATACCCAGGGAAGAAGCTGTTGCCGGAA |
| B6 and F6 | c370_2_50 | AATCACCTGTGAGTACCTGGATGAAGCATACCCAGGGAAGAAGCTGTTGA |
| G1 | s91_3 | AGGCCCCAAAT GGCTGGAAAT CTCGCCTATT TAGGCATTCT ACTCAGAAAA ACCTTAAAAA TTCACAAATG TGTCAGAAGA GCCTTGATGT GGAAACCGATA |
| G2 | s91_3_90 | ACAAATGGCTGGAAATCTCGCCTATTTAGGCATTCTACTCAGAAAAACCTTAAAAATTCACAAATGTGTCAGAAGAGCCTTGA TGTGGAA |
| G3 | s91_3_80 | AGGCTGGAAATCTCGCCTATTTAGGCATTCTACTCAGAAAAACCTTAAAAATTCACAAATGTGTCAGAAGAGCCTTGATA |
| G4 | s91_3_70 | AGAAATCTCGCCTATTTAGGCATTCTACTCAGAAAAACCTTAAAAATTCACAAATGTGTCAGAAGAGCCA |
| H1 | s91_3_60 | ACTCGCCTATTTAGGCATTCTACTCAGAAAAACCTTAAAAATTCACAAATGTGTCAGAAA |
| H2 | s91_3_50 | ACTATTTAGGCATTCTACTCAGAAAAACCTTAAAAATTCACAAATGTGTA |
| E1 | s97_4 | ATAGGAGGGG TGAAGCCCAG CTGCTCATGA ACGAGTTTGA GTCAGCCAAG GGTGACTTTG AGAAAGTGCT GGAAGTAAAC CCCCAGAATA AGGCTGCAAGA |
| E2 | s97_4_90 | AGGGGTGAAGCCCAGCTGCTCATGAACGAGTTTGAGTCAGCCAAGGGTGACTTTGAGAAAGTGCTGGAAGTAAACCCCCAGAA TAAGGCA |
| E3 | s97_4_80 | AGAAGCCCAGCTGCTCATGAACGAGTTTGAGTCAGCCAAGGGTGACTTTGAGAAGTGCTGGAAGTAAACCCCCAGAATA |
| E4 | s97_4_70 | ACCAGCTGCTCATGAACGAGTTTGAGTCAGCCAAGGGTGACTTTGAGAAAGTGCTGGAAGTAAACCCCCA |
| F1 | s97_4_60 | ATGCTCATGAACGAGTTTGAGTCAGCCAAGGGTGACTTTGAGAAAGTGCTGGAAGTAAAA |
| F2 | s97_4_50 | AATGAACGAGTTTGAGTCAGCCAAGGGTGACTTTGAGAAAGTGCTGGAAA |
| C5 | s74_3 | ATATGT AACTGAAGAA GGTGACAGTC CTTTGGGTGA CCATGTGGGT TCTCTGTCAG AGAAATTAGC AGCAGTCGTC AATAACCTAA ATACTGGGCA AGTGTA |
| C6 | s74_3_90 | AAACTGAAGAAGGTGACAGTCCTTTGGGTGACCATGTGGGTTCTCTGTCAGAGAAATTAGCAGCAGTCGTCAATAACCTAAAT ACTGGGA |
| C7 | s74_3_80 | AAAGAAGGTGACAGTCCTTTGGGTGACCATGTGGGTTCTCTGTCAGAGAAATTAGCAGCAGTCGTCAATAACCTAAATAA |
| C8 | s74_3_70 | AAGTGACAGTCCTTTGGGTGACCATGTGGGTTCTCTGTCAGAGAAATTAGCAGCAGTCGTCAATAACCTA |
| D5 | s74_3_60 | ACAGTCCTTTGGGTGACCATGTGGGTTCTCTGTCAGAGAAATTAGCAGCAGTCGTCAATA |
| D6 | s74_3_50 | ACTTTGGGTGACCATGTGGGTTCTCTGTCAGAGAAATTAGCAGCAGTCGA |

Example 5

Hybridization [33]P-Labeled cDNA Target with Oligo Glass ARRAY

1. Prepare a solution of 6×SSC buffer containing 0.1% SDS.
2. Place glass slide with printed oligo DNA in a hybridization chamber and add 2 ml of the solution prepared in step 1.
3. Prehybridize for 30 min at 60° C.
4. Mix labeled cDNA probe (Example 1, about 200 μl, total about 2-5×10$^6$ cpm) with 1/10th of the total volume (about 22 μl) of 10× denaturing solution (1 M NaOH, 10 mM EDTA) and incubate at 65° C. for 20 min. Then add 5 μl (1 μg/μl) of human Cot-1 DNA, and equal volume (about 225 μl) of 2× Neutralizing solution (1M NaHPO$_4$, pH 7.0) and continue incubating at 65° C. for 10 min.
5. Add the mixture prepared in Step 4 to the 2 ml of solution prepared in Step 1. Make sure that the two solutions are mixed together thoroughly.
6. Pour out the prehybridization solution and discard. Replace with the solution prepared in Step 5.
7. Hybridize overnight at 60° C.
8. Carefully remove the hybridization solution and discard in an appropriate container. Place the glass slides in a washing chamber with 20 ml of Wash Solution 1(2×SSC, 0.1% SDS). Wash the ARRAY for 10 min with continuous agitation at room temperature. Repeat this step four times.
9. Perform one additional 10-min wash in 20 ml of Wash Solution 2 (0.1×SSC, 0.1% SDS) with continuous agitation at room temperature.
10. Using forceps, remove the cDNA ARRAY from the container and shake excess the wash solution. Rinse with distilled water and let the array dry on air.
11. Expose the glass slide Array to X-ray film at –70° C. with an intensifying screen. Alternatively, use a phosphorimager (Molecular Dynamics).

Example 6

Assay for Hybridization Efficiency

Using the arrays and above protocols, the hybridization efficiency of each probe of different length on the array described in Example 4 was assayed using $^{32}$P labeled target complementary for each of the probes. The results of this assay are provided in FIG. 1. The results demonstrate that a significant increase in hybridization efficiency is achieved with oligonucleotide probes having a length greater than 50 nt.

It is evident from the above discussion that the subject arrays provide for a significant advance in the field. The subject invention provides for arrays of probes in which all of the probes on the array have substantially the same level of of high hybridization efficiency for their respective targets and exhibit a minimal level of non-specific hybridization. As such, the subject arrays eliminate the need for using multiple probe sequences for each target of interest or using mismatch control probes for each target, which is at least desired if not required with other array formats. In addition, the arrays are readily fabricated using non PCR based protocols, where the fabrication process is suitable for use in high throughput manufacturing. As such, the subject arrays combine the benefits of high throughput manufacturability of short oligonucleotide arrays with the benefits of high specificity observed in cDNA arrays. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

---

What is claimed is:

1. A nucleic acid hybridization assay comprising the steps of: contacting at least one labeled target nucleic acid sample with an array under conditions sufficient to produce a hybridization pattern; and detecting said hybridization pattern, wherein said array comprises at least one pattern of different probe oligonucleotide spots covalently attached to the surface of a solid support, wherein the spots on said array have a density of at least 10/cm2 and each probe oligonucleotide spot of said pattern comprises an oligonucleotide probe composition made up of long oligonucleotide probes ranging in length from 60 to about 100 nucleotides, and further wherein each oligonucleotide probe composition is made up of long oligonucleotide probes that have less than 50% homology with oligonucleotide probes of any other different probe composition of said array.

2. The method according to claim 1, wherein said method further comprises preparing said labeled target nucleic acid sample.

3. The method according to claim 2, wherein said preparing comprises conjugating a detectable label to a functionalized target nucleic acid.

4. The method according to claim 1, where said method further comprises: generating a second hybridization pattern; and comparing said hybridization patterns.

5. The method according to claim 1, wherein two or more different target nucleic acids hybridize to different probe oligonucleotide spots in said pattern.

6. The method according to claim 5, wherein each probe oligonucleotide spot in said pattern hybridizes to a different target nucleic acid.

7. The method according to claim 1, wherein the spots on said array do not exceed a density of $1000/cm^2$.

8. The method according to claim 1, wherein the spots on said array do not exceed a density of $400/cm^2$.

9. The method according to claim 1, wherein the spots on said array range from about 50 to 50,000 in number.

10. The method according to claim 1, wherein the spots on said array range from about 50 to 10,000 in number.

11. The method according to claim 1, wherein said solid support is glass.

12. The nucleic acid hybridization assay of claim 1, wherein said oligonucleotide probes are single-stranded.

13. The nucleic acid hybridization assay of claim 1, wherein said oligonucleotide probes range in length from 65 to 85 monomers.

* * * * *

UNITED STATES PATENT AND TRADEMARK OFFICE
CERTIFICATE OF CORRECTION

PATENT NO. : 7,556,919 B2
APPLICATION NO. : 10/985372
DATED : July 7, 2009
INVENTOR(S) : Alex Chenchik It is certified that error appears in the above-identified patent and that said Letters Patent is hereby corrected as shown below:

In Col. 25 and Col. 26, Table – 1, Array Position C1, replace the following probe sequence:

"AAACCCAGGA AAATACCAAA TCCAGATTTC TTTGAAGATC TGGAACCTTT CAGAATGACT CCTTTAGTG CTATTGGTTT GGAGCTGTGG TCCATGACCTA" with
AAACCCAGGA AAATACCAAA TCCAGATTTC TTTGAAGATC TGGAACCTTT CAGAATGACT CCTTTTAGTG CTATTGGTTT GGAGCTGTGG TCCATGACCTA

In Col. 25 and Col. 26, Table – 1, Array Position E3, replace the following probe sequence:

"AGAAGCCCAGCTGCTCATGAACGAGTTTGAGTCAGCCAAGGGTGACTTTGA GAAGTGCTGGAAGTAAACCCCCAGAATA" with
AGAAGCCCAGCTGCTCATGAACGAGTTTGAGTCAGCCAAGGGTGACTTT GAGAAAGTGCTGGAAGTAAACCCCCAGAATA

Signed and Sealed this

Sixth Day of October, 2009

David J. Kappos
*Director of the United States Patent and Trademark Office*

SEQUENCE LISTING

<160> NUMBER OF SEQ ID NOS: 38

<210> SEQ ID NO 1
<211> LENGTH: 293
<212> TYPE: DNA
<213> ORGANISM: Artificial Sequence
<220> FEATURE:
<223> OTHER INFORMATION: control s64 RNA

<400> SEQUENCE: 1

```
ggccaggata ccaaagcctt acaggacttc ctcctcagtg tgcagatgtg cccaggtaat      60
cgagacactt actttcacct gcttcagact ctgaagaggc tagatcggag ggatgaggcc     120
actgcactct ggtggaggct ggaggcccaa actaaggggt cacatgaaga tgctctgtgg     180
tctctccccc tgtacctaga aagctatttg agctggatcc gtccctctga tcgtgacgcc     240
ttccttgaag aatttcggac atctctgcca aagtcttgtg acctgtagct gcc            293
```

<210> SEQ ID NO 2
<211> LENGTH: 25
<212> TYPE: DNA
<213> ORGANISM: Artificial Sequence
<220> FEATURE:
<223> OTHER INFORMATION: gene-specific primer s64

<400> SEQUENCE: 2
cggccaggat accaaagcct tacag                                         25

<210> SEQ ID NO 3
<211> LENGTH: 101
<212> TYPE: DNA
<213> ORGANISM: Artificial Sequence
<220> FEATURE:
<223> OTHER INFORMATION: probe s64_2

<400> SEQUENCE: 3
acctagaaag ctatttgagc tggatccgtc cctctgatcg tgacgccttc cttgaagaat    60
ttcggacatc tctgccaaag tcttgtgacc tgtagctgcc a                      101

<210> SEQ ID NO 4
<211> LENGTH: 90
<212> TYPE: DNA
<213> ORGANISM: Artificial Sequence
<220> FEATURE:
<223> OTHER INFORMATION: probe s64_2_90

<400> SEQUENCE: 4
agaaagctat tgagctgga tccgtccctc tgatcgtgac gccttccttg aagaatttcg     60
gacatctctg ccaaagtctt gtgacctgta                                    90

<210> SEQ ID NO 5
<211> LENGTH: 80
<212> TYPE: DNA
<213> ORGANISM: Artificial Sequence
<220> FEATURE:
<223> OTHER INFORMATION: probe s64_2_80

<400> SEQUENCE: 5
agctatttga gctggatccg tccctctgat cgtgacgcct tccttgaaga atttcggaca    60
tctctgccaa agtcttgtga                                               80

<210> SEQ ID NO 6
<211> LENGTH: 70
<212> TYPE: DNA
<213> ORGANISM: Artificial Sequence
<220> FEATURE:
<223> OTHER INFORMATION: probe s64_2_70

<400> SEQUENCE: 6
atttgagctg gatccgtccc tctgatcgtg acgccttcct tgaagaattt cggacatctc    60
tgccaaagta                                                          70

<210> SEQ ID NO 7
<211> LENGTH: 60
<212> TYPE: DNA
<213> ORGANISM: Artificial Sequence
<220> FEATURE:
<223> OTHER INFORMATION: probe s64_2_60

<400> SEQUENCE: 7
agctggatcc gtccctctga tcgtgacgcc ttccttgaag aatttcggac atctctgcca    60

```
<210> SEQ ID NO 8
<211> LENGTH: 50
<212> TYPE: DNA
<213> ORGANISM: Artificial Sequence
<220> FEATURE:
<223> OTHER INFORMATION: probe s64_2_50

<400> SEQUENCE: 8
aatccgtccc tctgatcgtg acgccttcct tgaagaattt cggacatcta              50

<210> SEQ ID NO 9
<211> LENGTH: 101
<212> TYPE: DNA
<213> ORGANISM: Artificial Sequence
<220> FEATURE:
<223> OTHER INFORMATION: probe s62_2

<400> SEQUENCE: 9
aaacccagga aaataccaaa tccagatttc tttgaagatc tggaaccttt cagaatgact   60
ccttttagtg ctattggttt ggagctgtgg tccatgacct a                      101

<210> SEQ ID NO 10
<211> LENGTH: 90
<212> TYPE: DNA
<213> ORGANISM: Artificial Sequence
<220> FEATURE:
<223> OTHER INFORMATION: probe s62_2_90

<400> SEQUENCE: 10
aggaaaatac caaatccaga tttctttgaa gatctggaac ctttcagaat gactcctttt   60
agtgctattg gtttggagct gtggtccata                                    90

<210> SEQ ID NO 11
<211> LENGTH: 80
<212> TYPE: DNA
<213> ORGANISM: Artificial Sequence
<220> FEATURE:
<223> OTHER INFORMATION: probe s62_2_80

<400> SEQUENCE: 11
aataccaaat ccagatttct tgaagatct ggaacctttc agaatgactc cttttagtgc    60
tattggtttg gagctgtgga                                               80

<210> SEQ ID NO 12
<211> LENGTH: 70
<212> TYPE: DNA
<213> ORGANISM: Artificial Sequence
<220> FEATURE:
<223> OTHER INFORMATION: probe s62_2_70

<400> SEQUENCE: 12
aaaatccaga tttctttgaa gatctggaac ctttcagaat gactcctttt agtgctattg   60
gtttggagca                                                          70

<210> SEQ ID NO 13
<211> LENGTH: 60
<212> TYPE: DNA
<213> ORGANISM: Artificial Sequence
<220> FEATURE:
<223> OTHER INFORMATION: probe s62_2_60

<400> SEQUENCE: 13
acagatttct tgaagatct ggaacctttc agaatgactc cttttagtgc tattggttta    60
```

<210> SEQ ID NO 14
<211> LENGTH: 50
<212> TYPE: DNA
<213> ORGANISM: Artificial Sequence
<220> FEATURE:
<223> OTHER INFORMATION: probe s62_2_50

<400> SEQUENCE: 14
attctttgaa gatctggaac ctttcagaat gactcctttt agtgctatta                50

<210> SEQ ID NO 15
<211> LENGTH: 102
<212> TYPE: DNA
<213> ORGANISM: Artificial Sequence
<220> FEATURE:
<223> OTHER INFORMATION: probe c370_2

<400> SEQUENCE: 15
agggtcagct gatctacgag tctgccatca cctgtgagta cctggatgaa gcatacccag       60
ggaagaagct gttgccggat gacccctatg agaaagcttg ca                        102

<210> SEQ ID NO 16
<211> LENGTH: 90
<212> TYPE: DNA
<213> ORGANISM: Artificial Sequence
<220> FEATURE:
<223> OTHER INFORMATION: probe c370_2_90

<400> SEQUENCE: 16
aagctgatct acgagtctgc catcacctgt gagtacctgg atgaagcata cccagggaag       60
aagctgttgc cggatgaccc ctatgagaaa                                       90

<210> SEQ ID NO 17
<211> LENGTH: 80
<212> TYPE: DNA
<213> ORGANISM: Artificial Sequence
<220> FEATURE:
<223> OTHER INFORMATION: probe c370_2_80

<400> SEQUENCE: 17
aatctacgag tctgccatca cctgtgagta cctggatgaa gcatacccag ggaagaagct       60
gttgccggat gacccctata                                                  80

<210> SEQ ID NO 18
<211> LENGTH: 70
<212> TYPE: DNA
<213> ORGANISM: Artificial Sequence
<220> FEATURE:
<223> OTHER INFORMATION: probe c370_2_70

<400> SEQUENCE: 18
acgagtctgc catcacctgt gagtacctgg atgaagcata cccagggaag aagctgttgc       60
cggatgacca                                                             70

<210> SEQ ID NO 19
<211> LENGTH: 60
<212> TYPE: DNA
<213> ORGANISM: Artificial Sequence
<220> FEATURE:
<223> OTHER INFORMATION: probe c370_2_60

<400> SEQUENCE: 19

-continued

```
actgccatca cctgtgagta cctggatgaa gcatacccag ggaagaagct gttgccggaa      60
```

<210> SEQ ID NO 20
<211> LENGTH: 50
<212> TYPE: DNA
<213> ORGANISM: Artificial Sequence
<220> FEATURE:
<223> OTHER INFORMATION: probe c370_2_50

<400> SEQUENCE: 20

```
aatcacctgt gagtacctgg atgaagcata cccagggaag aagctgttga              50
```

<210> SEQ ID NO 21
<211> LENGTH: 102
<212> TYPE: DNA
<213> ORGANISM: Artificial Sequence
<220> FEATURE:
<223> OTHER INFORMATION: probe s91_3

<400> SEQUENCE: 21

```
aggcccaaa tggctggaaa tctcgcctat ttaggcattc tactcagaaa aaccttaaaa      60
attcacaaat gtgtcagaag agccttgatg tggaaaccga ta                      102
```

<210> SEQ ID NO 22
<211> LENGTH: 90
<212> TYPE: DNA
<213> ORGANISM: Artificial Sequence
<220> FEATURE:
<223> OTHER INFORMATION: probe s91_3_90

<400> SEQUENCE: 22

```
acaaatggct ggaaatctcg cctatttagg cattctactc agaaaaacct taaaaattca    60
caaatgtgtc agaagagcct tgatgtggaa                                    90
```

<210> SEQ ID NO 23
<211> LENGTH: 80
<212> TYPE: DNA
<213> ORGANISM: Artificial Sequence
<220> FEATURE:
<223> OTHER INFORMATION: probe s91_3_80

<400> SEQUENCE: 23

```
aggctggaaa tctcgcctat ttaggcattc tactcagaaa aaccttaaaa attcacaaat    60
gtgtcagaag agccttgata                                               80
```

<210> SEQ ID NO 24
<211> LENGTH: 70
<212> TYPE: DNA
<213> ORGANISM: Artificial Sequence
<220> FEATURE:
<223> OTHER INFORMATION: probe s91_3_70

<400> SEQUENCE: 24

```
agaaatctcg cctatttagg cattctactc agaaaaacct taaaaattca caaatgtgtc    60
agaagagcca                                                          70
```

<210> SEQ ID NO 25
<211> LENGTH: 60
<212> TYPE: DNA
<213> ORGANISM: Artificial Sequence
<220> FEATURE:
<223> OTHER INFORMATION: probe s91_3_60

<400> SEQUENCE: 25

```
actcgcctat ttaggcattc tactcagaaa aaccttaaaa attcacaaat gtgtcagaaa    60
```

<210> SEQ ID NO 26
<211> LENGTH: 50
<212> TYPE: DNA
<213> ORGANISM: Artificial Sequence
<220> FEATURE:
<223> OTHER INFORMATION: probe s91_3_50

<400> SEQUENCE: 26

```
actatttagg cattctactc agaaaaacct taaaaattca caaatgtgta               50
```

<210> SEQ ID NO 27
<211> LENGTH: 101
<212> TYPE: DNA
<213> ORGANISM: Artificial Sequence
<220> FEATURE:
<223> OTHER INFORMATION: probe s97_4

<400> SEQUENCE: 27

```
ataggagggg tgaagcccag ctgctcatga acgagtttga gtcagccaag ggtgactttg    60
agaaagtgct ggaagtaaac ccccagaata aggctgcaag a                       101
```

<210> SEQ ID NO 28
<211> LENGTH: 90
<212> TYPE: DNA
<213> ORGANISM: Artificial Sequence
<220> FEATURE:
<223> OTHER INFORMATION: probe s97_4_90

<400> SEQUENCE: 28

```
aggggtgaag cccagctgct catgaacgag tttgagtcag ccaagggtga ctttgagaaa    60
gtgctggaag taaacccca gaataaggca                                      90
```

<210> SEQ ID NO 29
<211> LENGTH: 80
<212> TYPE: DNA
<213> ORGANISM: Artificial Sequence
<220> FEATURE:
<223> OTHER INFORMATION: probe s97_4_80

<400> SEQUENCE: 29

```
agaagcccag ctgctcatga acgagtttga gtcagccaag ggtgactttg agaaagtgct    60
ggaagtaaac ccccagaata                                                80
```

<210> SEQ ID NO 30
<211> LENGTH: 70
<212> TYPE: DNA
<213> ORGANISM: Artificial Sequence
<220> FEATURE:
<223> OTHER INFORMATION: probe s97_4_70

<400> SEQUENCE: 30

```
accagctgct catgaacgag tttgagtcag ccaagggtga ctttgagaaa gtgctggaag    60
taaacccca                                                            70
```

<210> SEQ ID NO 31
<211> LENGTH: 60
<212> TYPE: DNA
<213> ORGANISM: Artificial Sequence
<220> FEATURE:
<223> OTHER INFORMATION: probe s97_4_60

```
<400> SEQUENCE: 31
atgctcatga acgagtttga gtcagccaag ggtgactttg agaaagtgct ggaagtaaaa    60

<210> SEQ ID NO 32
<211> LENGTH: 50
<212> TYPE: DNA
<213> ORGANISM: Artificial Sequence
<220> FEATURE:
<223> OTHER INFORMATION: probe s97_4_50

<400> SEQUENCE: 32
aatgaacgag tttgagtcag ccaagggtga ctttgagaaa gtgctggaaa              50

<210> SEQ ID NO 33
<211> LENGTH: 102
<212> TYPE: DNA
<213> ORGANISM: Artificial Sequence
<220> FEATURE:
<223> OTHER INFORMATION: probe s74_3

<400> SEQUENCE: 33
atatgtaact gaagaaggtg acagtccttt gggtgaccat gtgggttctc tgtcagagaa    60
attagcagca gtcgtcaata acctaaatac tgggcaagtg ta                      102

<210> SEQ ID NO 34
<211> LENGTH: 90
<212> TYPE: DNA
<213> ORGANISM: Artificial Sequence
<220> FEATURE:
<223> OTHER INFORMATION: probe s74_3_90

<400> SEQUENCE: 34
aaactgaaga aggtgacagt cctttgggtg accatgtggg ttctctgtca gagaaattag    60
cagcagtcgt caataaccta aatactggga                                    90

<210> SEQ ID NO 35
<211> LENGTH: 80
<212> TYPE: DNA
<213> ORGANISM: Artificial Sequence
<220> FEATURE:
<223> OTHER INFORMATION: probe s74_3_80

<400> SEQUENCE: 35
aaagaaggtg acagtccttt gggtgaccat gtgggttctc tgtcagagaa attagcagca    60
gtcgtcaata acctaaataa                                               80

<210> SEQ ID NO 36
<211> LENGTH: 70
<212> TYPE: DNA
<213> ORGANISM: Artificial Sequence
<220> FEATURE:
<223> OTHER INFORMATION: probe s74_3_70

<400> SEQUENCE: 36
aagtgacagt cctttgggtg accatgtggg ttctctgtca gagaaattag cagcagtcgt    60
caataaccta                                                          70

<210> SEQ ID NO 37
<211> LENGTH: 60
<212> TYPE: DNA
<213> ORGANISM: Artificial Sequence
<220> FEATURE:
<223> OTHER INFORMATION: probe s74_3_60
```

```
<400> SEQUENCE: 37
acagtccttt gggtgaccat gtgggttctc tgtcagagaa attagcagca gtcgtcaata        60

<210> SEQ ID NO 38
<211> LENGTH: 50
<212> TYPE: DNA
<213> ORGANISM: Artificial Sequence
<220> FEATURE:
<223> OTHER INFORMATION: probe s74_3_50

<400> SEQUENCE: 38
actttgggtg accatgtggg ttctctgtca gagaaattag cagcagtcga                    50
```